(12) United States Patent
Wang et al.

(10) Patent No.: US 11,130,766 B2
(45) Date of Patent: Sep. 28, 2021

(54) DEUTERATED THIENOPIPERIDINE DERIVATIVES, MANUFACTURING METHOD, AND APPLICATION THEREOF

(71) Applicant: JIANGSU TASLY DIYI PHARMACEUTICAL CO., LTD., Jiangsu (CN)

(72) Inventors: Guocheng Wang, Tianjin (CN); Jun Zhong, Tianjin (CN); Xueyu Xu, Tianjin (CN)

(73) Assignee: JIANGSU TASLY DIYI PHARMACEUTICAL CO., LTD., Jiangsu (CN)

( * ) Notice: Subject to any disclaimer, the term of this patent is extended or adjusted under 35 U.S.C. 154(b) by 98 days.

(21) Appl. No.: 15/739,337

(22) PCT Filed: Jun. 21, 2016

(86) PCT No.: PCT/CN2016/086538
§ 371 (c)(1),
(2) Date: Dec. 22, 2017

(87) PCT Pub. No.: WO2016/206576
PCT Pub. Date: Dec. 29, 2016

(65) Prior Publication Data
US 2018/0179222 A1 Jun. 28, 2018

(30) Foreign Application Priority Data
Jun. 23, 2015 (CN) .......................... 201510352739.3

(51) Int. Cl.
| | | |
|---|---|---|
| *C07D 495/04* | (2006.01) | |
| *C07F 9/6561* | (2006.01) | |
| *A61K 31/675* | (2006.01) | |
| *A61K 31/4535* | (2006.01) | |
| *A61P 9/00* | (2006.01) | |

(52) U.S. Cl.
CPC ........ *C07D 495/04* (2013.01); *A61K 31/4535* (2013.01); *A61K 31/675* (2013.01); *A61P 9/00* (2018.01); *C07F 9/6561* (2013.01); *C07B 2200/05* (2013.01); *C07B 2200/07* (2013.01)

(58) Field of Classification Search
CPC .................................................. C07D 495/04
See application file for complete search history.

(56) References Cited

U.S. PATENT DOCUMENTS

| | | | |
|---|---|---|---|
| 4,529,596 A | 7/1985 | Aubert et al. | |
| 4,740,510 A | 4/1988 | Badorc et al. | |
| 4,847,265 A | 7/1989 | Badorc et al. | |
| 5,190,938 A | 3/1993 | Badorc et al. | |
| 6,221,335 B1 * | 4/2001 | Foster | 424/1.81 |
| 6,429,210 B1 | 8/2002 | Bousquet et al. | |
| 6,440,710 B1 * | 8/2002 | Keinan et al. | 435/148 |
| 6,603,008 B1 * | 8/2003 | Ando et al. | 546/269.7 |
| 7,517,990 B2 * | 4/2009 | Ito et al. | 546/184 |
| 2007/0082929 A1 * | 4/2007 | Gant et al. | 514/338 |
| 2007/0197695 A1 * | 8/2007 | Potyen et al. | 524/110 |
| 2009/0203729 A1 | 8/2009 | Inoue et al. | |
| 2014/0038924 A1 | 2/2014 | Kumar et al. | |

FOREIGN PATENT DOCUMENTS

| | | |
|---|---|---|
| CN | 101591344 A | 12/2009 |
| CN | 101885730 A | 11/2010 |
| CN | 102120744 A | 7/2011 |
| CN | 103554132 A | 2/2014 |
| CN | 103665042 A | 3/2014 |
| CN | 104418891 A | 3/2015 |
| CN | 104447867 A | 3/2015 |
| CN | 107698620 A | 2/2018 |
| JP | 10-310586 A | 11/1998 |
| RU | 2184547 C2 | 7/2002 |
| RU | 2011105422 A | 8/2012 |
| WO | WO 1997/049397 A1 | 12/1997 |
| WO | WO 2008/157563 A2 | 12/2008 |

(Continued)

OTHER PUBLICATIONS

Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982.*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*

(Continued)

*Primary Examiner* — Brian E McDowell
(74) *Attorney, Agent, or Firm* — BakerHostetler

(57) ABSTRACT

The present invention discloses deuterated thienopiperidine derivatives, a manufacturing method and an application thereof. The deuterated thienopiperidine derivatives in the present invention are of a structure of the following formula (I). The present invention also comprises the application of the deuterated thienopiperidine derivatives as a drug for treating and preventing cardiovascular and cerebrovascular diseases.

Formula (I)

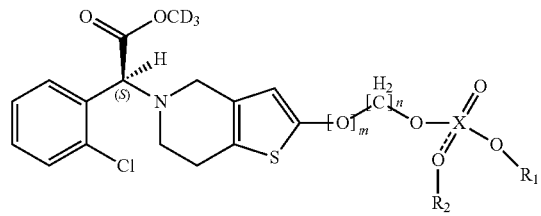

4 Claims, 1 Drawing Sheet

(56) References Cited

FOREIGN PATENT DOCUMENTS

| WO | WO 2011/079407 A1 | 7/2011 |
|---|---|---|
| WO | WO 2011/095049 A1 | 8/2011 |
| WO | WO 2014/043895 A | 3/2014 |
| WO | WO 2015/039577 A1 | 3/2015 |

OTHER PUBLICATIONS

Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol. 1999; 39: 817-825.*
Honma et al., Drug Metab Dispos 15 (4): 551 (1987).*
Geiger et al.; "Specific Impairment of Human Platelet P2YacADP Receptor-Mediated Signaling by the Antiplatelet"; Arterioscler Throm Vasc Biol., 1999, 19(8): p. 2007-2011.
Lemesle et al.; "Impact of high loading and maintenance dose of clopidogrel within the first 15 days after percutaneous coronary intervention on patient outcome"; American Heart Journal; Feb. 2009, 157(2): p. 375-382.
International Patent Application No. PCT/CN2016/086538; Written Opinion and the Search Report; dated Sep. 28, 2016; 7 pages.
Hosokawa; "Structure and Catalytic Properties of Carboxylesterase Isozymes Involved in Metabolic Activation of Prodrugs"; Molecules; vol. 13; 2008; p. 412-431.
Zhu et al.; "Carboxylesterase 1 as a determinant of clopidogrel metabolism and activation"; American Society for Pharmacology and Experimental Therapeutics; 2012; 35 pages.
Taketani et al.; "Carboxylesterase in the liver and small intestine of experimental animals and human"; Life Sci. vol. 81(11); Aug. 2007; p. 924-932.
Kazui et al.; "Identification of the Human Cytochrome P450 Enzymes Involved in the Two Oxidative Steps in the Bioactivation of Clopidogrel to its Pharmacologically Active Metabolite"; American Society of Pharmacology and Experimental Therapeutics; 2009; 42 pages.
U.S. Appl. No. 14/045,505, filed Oct. 3, 2013, Kumar et al.
Hagihara et al., "Comparison of Human Cytochrome P450 Inhibition by the Thienopyridines Prasugrel, Clopidogrel, and Ticlopidine"; Drug Metabolism and Pharmacokinetics, 2008, vol. 23 No. 6; p. 412-420.
Tuffal et al., "An Improved Method for Specific and Quantitative Determination of the Clopidogrel Active Metabolite Isomers in Human Plasma"; Thrombosis and Haemostasis, 2011, vol. 105 No. 4; p. 696-705.
Farid, et al., "The Disposition of Prasugrel, a Novel Thienopyridine, in Humans"; Drug Metabolism & Disposition, 2007, vol. 35 No. 7; p. 1096-1104.
Pereillo et al., "Structure and Stereochemistry of the Active Metabolite of Clopidogrel," Drug Metabolism & Disposition, 2002, vol. 30 No. 11; p. 1288-1295.
Cardinal et al., "The Electronic Aggregometer: A Novel Device for Assessing Platelet Behavior in Blood"; Journal of Pharmacological Methods, 1980, vol. 3; p. 135-158.
Schumacher et al., "Biomarker Optimization to Track the Antithrombotic and Hemostatic Effects of Clopidogrel in Rats"; Journal of Pharmacology and Experimental Therapeutics, 2007, vol. 322 No. 1, p. 369-377.
Tanaka et al., "Z-335, a New Thromboxane A2 Receptor Antagonist, Prevents Arterial Thrombosis Induced by Ferric Chloride in Rats"; European Journal of Pharmacology, 2000, vol. 401, p. 413-418.
Borisy et al., "Systematic Discovery of Multicomponent Therapeutics", PNAS 2003, 100, p. 7977-7982.
European Medicines Agency, "CHMP Assessment Report for DuoPiavin International Nonproprietary Name: Clopidogrel/Acetylsalicylic Acid", Doc. Ref: EMA/CHMP/196090/2010 Dec. 17, 2009, 37 pages.
Farid et al., "Metabolism and Disposition of the Thienopyridine Antiplatelet Drugs Ticlopidine, Clopidogrel, and Prasugrel in Humans", The Journal of Clinical Pharmacology, 2010, 50, p. 126-142.
Hagihara et al., "A Possible Mechanism for the Differences in Efficiency and Variability of Active Metabolite Formation from Thienopyridine Antiplatelet Agents, Prasugrel and Clopidogrel", Drug Metabolism and Disposition, 2009, 37(11), p. 2145-2152.
Hornfeldt, "Tautomeric Properties and Some Reactions of the 2-Hydroxythiophene and the 2-Hydroxyfuran Systems", Svensk Kemisk Tidskrift, 1968, 80(10), p. 343-356.
Kazui et al., "Identification of the Human Cytochrome P450 Enzymes Involved in the Two Oxidative Steps in the Bioactivation of Clopidogrel to Its Pharmacologically Active Metabolite", Drug Metabolism and Disposition, 2010, 38(1), p. 92-99.
Maffrand, "The Story of Clopidogrel and Its Predecessor, Ticlopidine: Could These Major Antiplatelet and Antithrombotic Drugs be Discovered and Developed Today?", C.R. Chimie, 2012, 15, p. 737-743.
Nguyen et al., "Resistance to Clopidogrel: A Review of the Evidence", Journal of the American College of Cardiology, 2005, 45(8), p. 1157-1164.
Nishiya et al., "Mechanism-Based Inhibition of Human Cytochrome P450 2B6 by Ticlopidine, Clopidogrel, and the Thiolactone Metabolite of Prasugrel", Drug Metabolism and Disposition, 2009, 37(3), 589-593.
Velder et al., "A Scalable Synthesis of (+−.)-2-Oxoclopidogrel"; Synlett, 2010, 3, p. 467-469.
West, "Solid State Chemistry and its Applications", Wiley, New York, 1988, 358 & 365.
Zimmermann et al., "Multi-Target Therapeutics: When the Whole is Greater Than the Sum of the Parts", Drug Discovery Today, 2007, 12, p. 34-42.
Dahl et al.; "Implications of Inter-Individual Differences in Clopidogrel Metabolism, with Focus Pharmacogenetics"; Pharmaceuticals; vol. 3; 2010; p. 782-794.
N. Pandit; "Introduction to the pharmaceutical sciences"; Lippincott, Williams and Wilkins Baltimore; 2006; p. 19.
Before the Patent Trial and Appeal Board; *Ashok Kumar et al.* v. *93g et al.*; Patent Interference No. 106,039; dated Sep. 9, 2016; 34 pages.
K. Morrison; "Physical Science—Level 3"; Pearson Education, Capetown; 2008; p. 16-18.
"PubChem SD File Formatted Data V2.0.1" Oct. 17, 2011; 14 pages.
"PubChem Upload Help Document (complete version)"; online https://pubchem.ncbi.nlm.nih.gov/upload/docs/upload_help_complete.html; accessed Aug. 24, 2018; 40 pages.
Online https://pubchemdocs.ncbi.nlm.nih.gov/substances; accessed Aug. 24, 2018.
Pubchem Database entry ZINC22065576 Deposit Date: May 28, 2009 Available Date: May 28, 2009, Online "https:// pubchem.ncbi.nlm.nih.gov/substance/62688539" accessed Jun. 5, 2017; 5 pages.
Online "https://pubchem.ncbi.nlm.nih.gov/compound/29986184" accessed Jun. 5, 2017; 11 pages.
Online "https://pubchem.ncbi.nlm.nih.gov/source/ZINC" accessed Jun. 5, 2017.
Elguero et al.; "Prototropic Tautomerism of Heterocycles: Heteroaromatic Tautomerism—General Overview and Methodology"; Advances in Heterocyclic Chemistry; 2000, 76, p. 1-64.
Loudon "Organic Chemistry" 3rd Edition 1995, Benjamin/Cummings Publishing, Redwood City, CA pp. 242-243.
"Happy Birthday!" Chromatographia 2008, 67, January (No. 1 / 2).
US Food and Drug Administration "Development of New Stereoisomeric Drugs" Publication Date: May 1, 1992; 6 pages.
Aboul-Enein, H. Y. editor, "Separation Techniques in Clinical Chemistry" 2003, Marcel Dekker pp. 158-159.
Beauchamp; "Chem 315/316 Keto-Enol Tautomer Handout"; University of California Pomona Jan. 25, 2011; 24 pages.
Wainer, Irving P.; "Drug Stereochemistry: analytical methods and pharmacology" Macel Dekker New York: 1993, pp. 29-30.
Harrold et al.; "Medicinal Chemistry" ASHP: Bethesda, 2013, Chapter 7; 4 pages.

(56) References Cited

OTHER PUBLICATIONS

Kozma; "CRC handbook of optical resolutions via diastereomeric salt formation" CRC press: 2002, p. 3-5.
Savi et al.; "Identification and Biological Activity of the Active Metabolite of Clopidogrel."; Thromb Haemost; 2000; 84; p. 891-896.
Testa et al.; "The Biochemistry of Drug Metabolism—An Introduction Part 5. Metabolism and Bioactivity"; Chemistry & Biodiversity—vol. 6, 2009, p. 591-683.
U.S. Appl. No. 14/045,505; Non-Final Office Action; dated May 12, 2015; 36 pages.
Rosenfeld; "Basic Skill for Organic Chemistry: A Toolkit" 1998, p. 52.
Lin et al.; "Overview of Chirality and Chiral Drugs"; Chiral Drugs: Chemistry and Biological Action; Chapter 1 First Edition; 2011; p. 3-28.
*Sanofi-Synthelavo* v. *Apotex Inc.*; U.S. Court of Appeals; 89 USPQ2d 1370; Bloomberg BNA (2008) No. 2007-1438; dated Dec. 12, 2008; 3 pages.
"Declaration—B.d.R.203(b)"; United States Patent and Trademark Office Before the Patent Trial and Appeal Board, Patent Interference No. 106,029; dated Jun. 2, 2015; 29 pages.
Anderson et al., "Personalized Approaches to Clopidogrel Therapy: Are We There Yet?"; American Stroke Association, 2010, vol. 41, No. 12, p. 2997-3002.
Berger et al., "Antiplatelet Therapy: The Role of Platelet Function Testing"; at http://www.theHeart.org/documents/sitestructure/en/content/programs/11614-29/1161429.html, 2011, p. 1-15.
Brandt, et al., "A Comparison of Prasugrel and Clopidogrel Loading Doses on Platelet Function: Magnitude of Platelet Inhibition is Related to Active Metabolite Formation"; American Heart Journal, 2007, vol. 153, No. 1, p. 66e9-66e16.
Dib et al., "A New Era for Antiplatelet Therapy in Patients with Acute Coronary Syndrome"; The American Journal of the Medical Sciences, 2010, vol. 340, No. 5, p. 407-411.
Giusti et al., "Response to Antiplatelet Treatment: From Genes to Outcome"; The Lancet, 2010, vol. 376, No. 9749, p. 1278-1281.
Hagihara et al., "A Possible Mechanism for the Differences in Efficiency and Variability of Active Metabolite Formation from Thienopyridine Antiplatelet Agents, Prasugrel and Clopidogrel"; Drug Metabolism and Disposition, 2009; vol. 37, No. 11, p. 2145-2152.
Von Beckerath et al., "Absorption, Metabolization, and Antiplatelet Effects of 300-, 600-, and 900-mg Loading Doses of Clopidogrel: Results of the ISAR-CHOICE (Intracoronary Stenting and Antithrombotic Regimen: Choose Between 3 High Oral Doses for Immediate Clopidogrel Effect) Trial"; Circulations, 2005, vol. 112, No. 19, p. 2946-2950.
Ingelman-Sunberg et al., "Genetic Polymorphism and Toxicology—with Emphasis on Cytochrome P450"; Toxicological Sciences, 2010, p. 1-30.
Mannheimer et al., "Drug-Drug Interactions that Reduce the Formation of Pharmacologically Active Metabolites: A Poorly Understood Problem in Clinical Practice"; Journal of Internal Medicine, 2010, vol. 268, No. 6, p. 540-548.
Mega et al., "Reduced-Function CYP2C19 Genotype and Risk of Adverse Clinical Outcomes Among Patients Treated with Clopidogrel Predominantly for PCI: A Meta-Analysis"; Journal of the American Medical Association, 2010, vol. 304, No. 16, p. 1821-1830.
Plavix Label, Highlights of Prescribing Information; Aug. 2010; 25 pages.
Achar et al., "Pharmacokinetics Drug Metabolism, and Safety of Prasugrel and Clopidogrel"; Postgraduate Medicine, 2011, vol. 123, No. 1, pp. 73-79.
Angiolillo et al., "High Clopidogrel Loading Dose during Coronary Stenting: Effects on Drug Response and Interindividual Variability"; European Heart Journal, 2004, vol. 25, p. 1903-1910.
Bouman et al., "Paraoxonase-1 is a Major Determinant of Clopidogrel Efficacy"; Nature Medicine, 2011, vol. 17, No. 1, p. 110-116.
Cadroy et al., "Early Potent Antithrombotic Effect With Combined Aspirin and a Loading Dose of Clopidogrel on Experimental Arterial Thrombogenesis in Humans"; American Heart Association, Circulation, 2000, vol. 101, p. 2823-2828.
Caplain et al., "Pharmacokinetics of Clopidogrel"; Seminars in Thrombosis and Hemostasis, 1999, vol. 25, Suppl. 2, Georg Thieme Verlag Stuttgart, NY (publisher), p. 25-28.
Cattaneo, Marco; "Fast, potent, and reliable inhibition of platelet aggregation"; European Heart Journal Supplements, 2009, vol. 11, Supplement G, pp. G9-G13.
Conrado et al., "Role of drug absorption in the pharmacokinetics of therapeutic interventions for stroke"; Annals of the New York Academy of Sciences, 2010, vol. 1207, p. 134-142.
Curzen et al., "Monitoring the effectiveness of antiplatelet therapy: opportunities and limitations"; an accepted article for British Journal of Clinical Pharmacology, 2011, p. 1-39.
Damani et al., "The Case for Routine Genotyping in Dual-Antiplatelet Therapy"; Journal of the American College of Cardiology, 2010, vol. 56, No. 2, p. 109-111.
DiGirolamo et al., "Beyond Efficacy: Pharmacokinetic Differences Between Clopidogrel, Prasugrel and Ticagrelor"; Expert Opinion on Pharmacotherapy, 2011, p. 1-11.
Disney et al., "Review Article: Proton Pump Inhibitors with Clopidogrel-Evidence for and Against a Clinically-Important Interaction"; Alimentary Pharmacology & Therapeutics, 2011, vol. 33, No. 7, p. 758-767.
Fleisher et al., "Drug, Meal and Formulation Interactions Influencing Drug Absorption After Oral Administration: Clinical Implications"; Clinical Pharmacokinetics, 1999, vol. 36, No. 3, p. 233-254.
Furuta, Takahisa, "Risk and Benefit of Proton Pump Inhibitor for Patients Undergoing AntiPlatelet Therapy Including Clopidogrel"; Internal Medicine, 2009, vol. 48, p. 1847-1848.
Gurbel et al., "Clopidogrel Loading with Eptifibatide to Arrest the Reactivity of Platelets: Results of the Clopidogrel Loading with Eptifatide to Arrest the Reactivity of Platelets (Clear Platelets) Study"; American Heart Association, Circulation, 2005, vol. 111, p. 1153-1159.
Gurbel et al., "Randomized Double-Blind Assessment of the Onset and Offset of the Antiplatelet effects of Ticagrelor Versus Clopidogrel in Patients with Stable Coronary Artery Disease: The Onset/Offset Study"; Circulation Journal of the American Heart Association, 2009, vol. 120, p. 2577-2585 and Supplemental Material.
Hagihara et al., "Comparison of Formation of Thiolactones and Active Metabolites of Prasugrel and Clopidogrel in Rats and Dogs"; Xenobiotica, 2009, vol. 39, No. 3, p. 218-226.
Herbert et al., "Clopidogrel, A Novel Antiplatelet and Antithrombotic Agent"; Cardiovascular Drug Reviews, 1993, vol. 11, No. 2, p. 180-198.
Holmes et al., "ACCF/AHA Clopidogrel Clinical Alert: Approaches to the FDA "Boxed Warning": A Report of the American College of Cardiology Foundation Task Force on Clinical Expert Consensus Documents and the American Heart Association"; Circulation Journal of the American Heart Association, 2010, vol. 122, p. 537-557.
Husted et al., "Pharmacodynamics, pharmacokinetics, and safety of the oral reversible P2Y12 antagonist AZD6140 with aspirin in patients with atherosclerosis: a double-blind comparison to clopidogrel with aspirin"; European Heart Journal, 2006, vol. 27, p. 1038-1047.
Kim et al., "Bioequivalence and Tolerability of Two Clopidogrel Salt Preparations, Besylate and Bisulfate: A Randomized, Open-Label, Crossover Study in Healthy Korean Male Subjects"; Clinical Therapeutics, 2009, vol. 31, No. 4, p. 793-803.
Lins, "Pharmacokinetic Profile of 14C-Labeled Clopidogrel"; Seminars in Thrombosis and Hemostasis, 1999, vol. 25, Suppl. 2, p. 29-33.
Makkar et al., "Effects of clopidogrel, aspirin and combined therapy in a porcine ex vivo model of high-shear induced sten thrombosis"; European Heart Journal, 1999, vol. 19, p. 1538-1546.
Mohammad et al., "Antiplatelet Therapy After Placement of a Drug-Eluting Stent: A Review of Efficacy and Safety Studies"; Clinical Therapeutics, 2010, vol. 32, No. 14, p. 2265-2281.
Nishiya et al., "Comparison of mechanism-based inhibition of human cytochrome P450 2C19 by ticlopidine, clopidogrel, and prasugrel"; Xenoblotica, 2009, vol. 39, No. 11, pp. 836-843.

(56) References Cited

OTHER PUBLICATIONS

Sada et al., "The prophylactic use of a proton pump inhibitor (PPI) in patients treated with clopidogrel and aspirin for an acute coronary syndrome or placement of a coronary stent reduces the rate of upper gastrointestinal bleeding with no apparent increase in cardiovascular events"; Internal and Emergency Medicine, Mar. 3, 2011, 2 pages.

Savi et al., "The Antiaggregating Activity of Clopidogrel is due to a Metabolic Activation by the Hepatic Cytochrome P450-1A"; Thrombosis and Haemostasis, 1994, vol. 72, No. 2, p. 313-317.

Sciascio et al., "Effectiveness of In-Laboratory High-Dose Clopidogrel Loading Versus Routine Pre-Load in Patients Undergoing Percutaneous Coronary Intervention"; Journal of the American College of Cardiology, 2010, vol. 56, No. 7, pp. 550-557.

Takahashi et al., "Different Inhibitory Effects in Rat and Human Carboxylesterases"; Drug Metabolism and Desposition, 2009, vol. 37, p. 956-961.

Yan et al., "Variability in Response to Clopidogrel: How Important are Pharmacogenetics and Drug Interactions?"; British Journal of Clinical Pharmacology, 2011, 43 pages.

Zairis et al., "The impact of treatment with omeprazole on the effectiveness of clopidogrel drug therapy during the first year after successful coronary stenting"; Can. J. Cardio., 2010, vol. 26, No. 2, pp. e54-e57.

Terpening, Chris, "Clopidogrel: A Pharmacogenomic Perspective on its Use in Coronary Artery Disease"; Clinical Medicine Insights: Cardiology, 2010, vol. 4, pp. 117-128.

O'Donoghue et al., "Clopidogrel Response Variability and Future Therapies: Clopidogrel Does One Size Fit All?"; Circulation, 2006, vol. 114, p. e600-e606.

Kuliczkowski et al., "Interindividual variability in the response to oral antiplatelet drugs: a position paper of the Working Group on antiplatelet drugs resistance appointed by the Section of Cardiovascular Interventions of the Polish Cardiac Society, endorsed by the Working Group on Thrombosis of the European Society of Cardiology"; European Heart Journal, 2009, vol. 30, p. 426-435.

Angiolillo et al., "Variability in Individual Responsiveness to Clopidogrel,"; Journal of the American College of Cardiology, 2007, vol. 49, No. 14, p. 1505-1516.

Willett et al., "Thienopyridines in Acute Coronary Syndrome"; Annals of Pharmacotherapy, 2011, pp. 207-217.

Scott et al., "Identification of CYP2C19*4B: pharmacogenetic implications for drug metabolism including clopidogrel responsiveness"; The Pharmacogenomics Journal, 2011, p. 1-9.

Shand et al., "Ticagrelor: from concept to clinical evaluation"; Biomarks Med., 2011, vol. 5, No. 1, p. 53-62.

Sharma et al. "Aspirin and clopidogrel hyporesponsiveness and nonresponsiveness in patients with coronary artery stenting"; Vascular Health and Risk Management, 2009, vol. 5, p. 965-972.

Storey et al., "Incidence of Dyspnea and Assessment of Cardiac and Pulmonary Function in Patients with Stable Coronary Artery Disease Receiving Ticagrelor, Clopidogrel, or Placebo in the Onset/Offset Study"; Journal of the American College of Cardiology, 2010, vol. 56, No. 3, p. 185-193.

Suh et al., "Increased risk of atherothrombotic events associated with cytochrome P450 3A5 polymorphism in patients taking clopidogrel"; CMAJ, 2006, vol. 174, No. 12, p. 1715-1722.

Taubert et al., "Pharmacokinetics of clopidogrel after administration of a high loading dose"; Thrombosis and Haemostasis, 2004, vol. 92, No. 2, pp. 311-316.

Topol et al., "Catapulting clopidogrel pharmacogenomics forward"; Nature Medicine, 2011, vol. 17, No. 1, pp. 40-41.

Wallentin et al., "Ticagrelor versus Clopidogrel in Patients with Acute Coronary Syndromes"; The New England Journal of Medicine, 2009, vol. 361, No. 11, pp. 1045-1057.

White, Harvey, "Oral antiplatelet therapy for atherothrombotic disease: Current evidence and new directions"; American Heart Journal, 2011, vol. 161, No. 3, pp. 450-461.

Zafar et al., "Crushed Clopidogrel Administered via Nasogastric Tube Has Faster and Greater Absorption than Oral Whole Tablets"; Journal of Interventional Cardiology, 2009, vol. 22, No. 4, p. 385-389.

"Sun Exhibit 1025"; United States Patent and Trademark Office, PTAB, Interference No. 106,029; dated Oct. 15, 2015; 19 pages.

"Sun Substantive Motion 2"; United States Patent and Trademark Office, PTAB, Interference No. 106,029; dated Oct. 15, 2015; 31 pages.

Bouman et al., "Paraoxonase-1 is a Major Determinant of Clopidogrel Efficacy"; Nature Medicine, 2011, Supplementary Information; 46 pages.

* cited by examiner

DEUTERATED THIENOPIPERIDINE DERIVATIVES, MANUFACTURING METHOD, AND APPLICATION THEREOF

CROSS-REFERENCE TO RELATED APPLICATIONS

This application is the National Stage of International Application No. PCT/CN2016/086538, filed Jun. 21, 2016, which claims the benefit of Chinese application number 201510352739.3, filed Jun. 23, 2015 the disclosures of which are incorporated herein by reference in their entireties.

TECHNICAL FIELD

The present invention relates to the field of organic chemistry and medicinal chemistry. Particularly, the present invention relates to deuterated thienopiperidine derivatives; the present invention also relates to the pharmaceutically acceptable salts of deuterated thienopiperidine derivatives, a manufacturing method thereof, and an application thereof in the manufacturing of a drug for treating and preventing cardiovascular and cerebrovascular diseases.

BACKGROUND

Clopidogrel, a thienopyridine drug, can inhibit the platelet activity with high efficiency and is currently an anti-platelet drug that is widely used for acute coronary syndrome and treating patients receiving percutaneous coronary intervention (PCI). Its structural formula is present as follow:

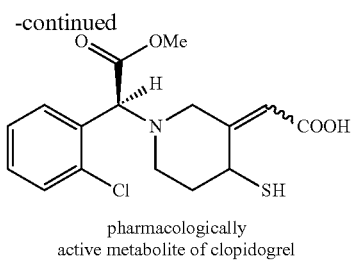

Clopidogrel

Clopidogrel is a pro-drug without activity, and needs to be converted to the active metabolite by the liver cytochrome P450 (CYP450 the metabolic process is present as follow:

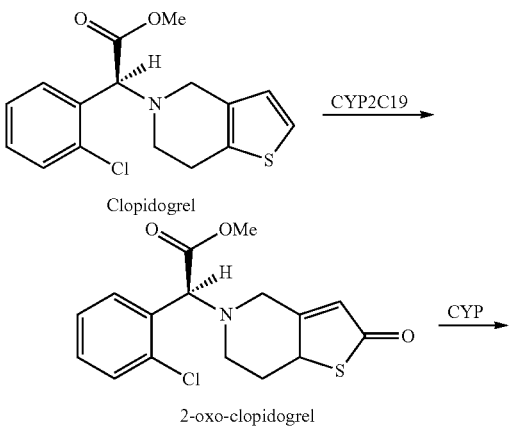

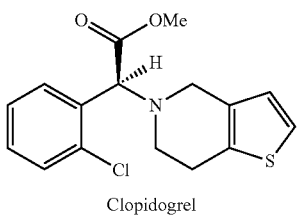 [SMILES: COC(=O)[C@H](c1ccccc1Cl)N1CCc2sccc2C1]

pharmacologically active metabolite of clopidogrel

This metabolite binds the adenosine diphosphate (ADP) receptor P2Y12 on the surface of the platelet membrane to play the role of blocking the binding between ADP and the platelet receptor and secondarily activating the ADP mediated glycoprotein GPIIbPIIIa complex, and thereby to inhibit the platelet aggregation (Arterio-scler Thromb Vase Biol, 1999, 19 (8): 2002-2011). Clopidogrel can substantially reduce the incidence of the formation of the subacute stent thrombosis, reducing the occurrence of death and cardiovascular events such as recurrent heart infarction. However, recent studies found that about 11%~44% (Am Heart J, 2009, 157 (2): 375-382.) patients showed low response or even no response to clopidogrel, and this phenomenon has been also called the "clopidogrel resistance".

China patent application 201310428052.4 discloses the thienopiperidine derivative with the following structure, which is a pro-drug of the 2-oxy-clopidogrel (metabolite of the clopidogrel), to improve the "clopidogrel resistance".

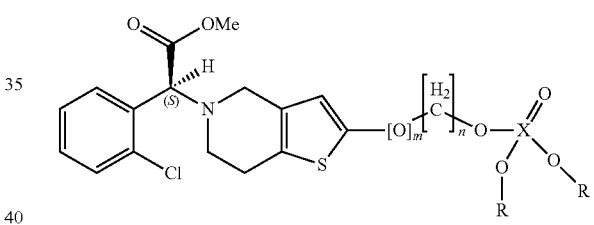

However, this series of compounds still have the disadvantages such as low inhibition rate of the platelet aggregation and high hydrolysis rate. In order to solve the disadvantages described above, develop new anti-platelet aggregation drugs with quick clinical onset, good therapeutic effect, and ability to avoid clopidogrel resistance, and find compounds which are advantageous to be formulated into a formulation so as to improve the bioavailability, reduce the side effects, and facilitate the dissolution, absorption, and administration, the present invention has developed a series of new deuterated thienopiperidine derivatives, a manufacturing method and an application thereof. China patent application 201310428052.4 is entirely incorporated into the present application by reference.

SUMMARY OF THE INVENTION

The technical problem to be solved by the present invention is to overcome disadvantages described above, design and synthesize new optically active deuterated thienopiperidine derivatives, thereby to develop an anti-platelet aggregation drug with good therapeutic effect and low side effect.

Specifically, one objective of the present invention is to provide optically active deuterated thienopiperidine derivatives or the pharmaceutically acceptable salt, solvate, polymorph, enantiomer or racemic mixture thereof. Another objective of the present invention is to provide a manufacturing method for optically active deuterated thienopiperidine derivatives or the pharmaceutically acceptable salt, solvate, polymorph, enantiomer or racemic mixture or the pharmaceutical composition thereof.

Another objective of the present invention is to provide a pharmaceutical composition with optically active deuterated thienopiperidine derivatives or the pharmaceutically acceptable salt, solvate, polymorph, enantiomer or racemic mixture or the pharmaceutical composition thereof as the active component.

Still another objective of the present invention is to provide a use of optically active deuterated thienopiperidine derivatives or the pharmaceutically acceptable salt, solvate, polymorph, enantiomer or racemic mixture or the pharmaceutical composition thereof in the manufacturing drugs.

One more objective of the present invention is to provide a method for treating related diseases with optically active deuterated thienopiperidine derivatives or the pharmaceutically acceptable salt, solvate, polymorph, enantiomer or racemic mixture or the pharmaceutical composition thereof or by using the pharmaceutical composition.

To accomplish the above objectives, the technical solutions employed by the present invention are present as follow:

The present invention provides optically active deuterated thienopiperidine derivatives of formula (I) or the pharmaceutically acceptable salt, solvate, polymorph, enantiomer or racemic mixture thereof:

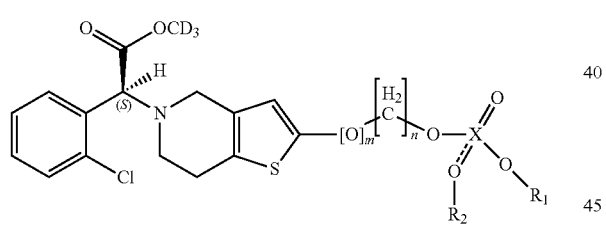

Formula (I)

wherein, D in $CD_3$ is deuterium, which is a stable isotope of hydrogen, also called as heavy hydrogen; X is P or S; m is 0 or 1; n is 0 or 1; $R_1$ is selected from hydrogen, C1-C4 linear or branched alkyl which is substituted or unsubstituted with halogen, phenyl or substituted phenyl; $R_2$ is unsubstituted or is selected from hydrogen, C1-C4 linear or branched alkyl which is substituted or unsubstituted with halogen, phenyl or substituted phenyl, wherein when $R_2$ is unsubstituted, X and O form a double bond.

Preferably, wherein X is P, m is 0, n is 0, $R_1$ is selected from hydrogen, $CH_3$—, $CH_3CH_2$—, isopropyl, $CCl_3CH_2$—, and phenyl; $R_2$ is selected from hydrogen, $CH_3$—, $CH_3CH_2$—, isopropyl, $CCl_3CH_2$—, and phenyl.

Or, wherein X is P, m is 1, n is 1, $R_1$ is selected from hydrogen, $CH_3$—, $CH_3CH_2$—, isopropyl, $CCl_3CH_2$—, tert-butyl, and phenyl; $R_2$ is selected from hydrogen, $CH_3$—, $CH_3CH_2$—, isopropyl, $CCl_3CH_2$—, tert-butyl, and phenyl.

Or, wherein X is S, m is 0, n is 0, $R_1$ is selected from hydrogen, $CH_3$—, $CH_3CH_2$—, isopropyl, $CCl_3CH_2$—, tert-butyl, and phenyl; $R_2$ is unsubstituted, and X and O form a double bond.

Deuterated thienopiperidine derivatives of the present invention are preferably the following compounds:

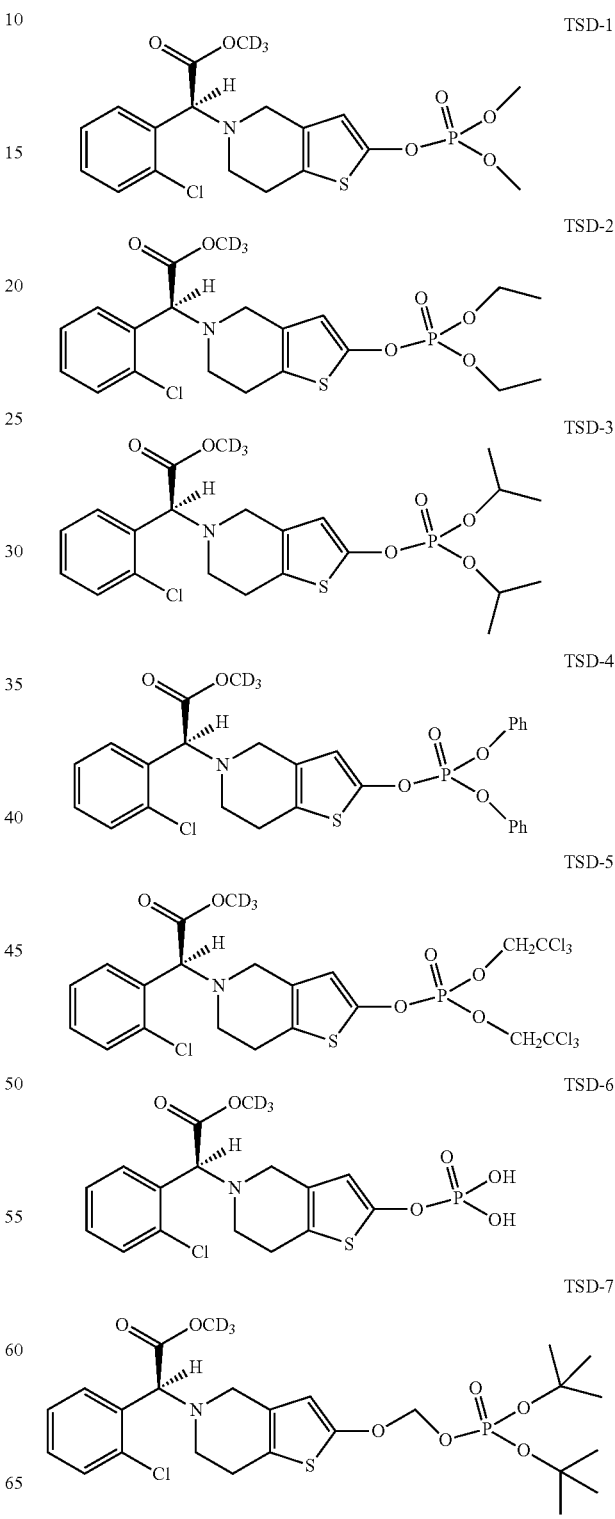

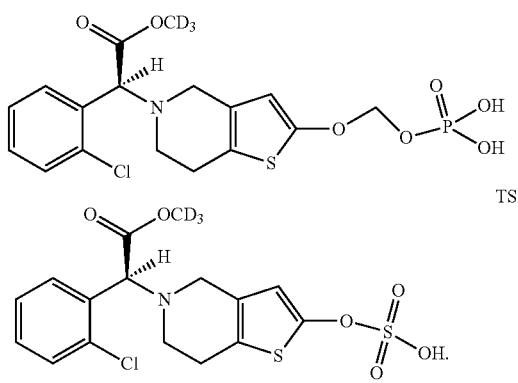

TSD-8

TSD-9

The present invention also comprises the pharmaceutically acceptable salt of deuterated thienopiperidine derivatives, wherein the salt can be a salt formed by deuterated thienopiperidine derivatives with sulfuric acid, hydrochloric acid, hydrobromic acid, phosphoric acid, tartaric acid, fumaric acid, maleic acid, citric acid, acetic acid, formic acid, methanesulfonic acid, p-toluenesulfonic acid, oxalic acid or succinic acid.

The present invention also provides a pharmaceutical composition, which comprises deuterated thienopiperidine derivatives or the pharmaceutically acceptable salt thereof described by the present invention. The pharmaceutical composition can also comprise a pharmaceutically acceptable carrier as desired. The pharmaceutically acceptable inert carrier can be in the solid state or liquid state. Powders, tablets, dispersible powders, capsules, suppositories and ointment-like solid or semi-solid pharmaceutical formulations can be prepared, and in that case a solid carrier is usually used. The solid carrier which may be used is preferably one or more substances selected from diluents, flavoring agents, solubilizers, lubricants, suspending agents, binders, and swelling agents etc., or may be an encapsulating material. In the powdered formulation, the carrier contains 5%-70% of the micronized active ingredient. Specific examples of appropriate solid carriers include magnesium carbonate, magnesium stearate, talc, sucrose, lactose, pectin, dextrin, starch, gelatin, tragacanth gum, methyl cellulose, carboxymethyl cellulose sodium, low boiling wax, and cocoa butter, etc. Due to easy administration, tablets, powders, and capsules represent the oral solid formulations which are most advantageous for absorption. The liquid formulation includes solution, suspension and emulsion. For example, the injectable formulation for parenteral administration can use water or mixed solution of water and propylene glycol, and its physiological conditions such as isotonic degrees and pH suitable for the living body are adjusted. The liquid formulation can also be formulated into the an aqueous polyethylene glycol solution. An oral aqueous solution can be prepared by dissolving the active ingredient in the water, followed by addition of appropriate colorants, flavoring agents, stabilizers and thickening agents. The micronized active ingredient can be dispersed in a viscous material, such as natural or synthetic rubber, methyl cellulose, sodium carboxymethyl cellulose and other known suspending agents, to prepare an oral aqueous suspension.

For the easy administration and dose evenness, it is particularly advantageous for the above pharmaceutical formulation to be formulated into unit dosage form. The unit dosage form of a formulation refers to the physically detachable unit suitable as a single dose, with each unit containing a predetermined amount of the active ingredient calculated to give the desired therapeutic effect. This unit dosage form can be a packaged form, for example, tablets, capsules, powders packaged in a tubule or vial, or ointments, gels or creams packaged in a tube or bottle.

Although the quantity of the active ingredient in the unit dosage form may vary, it is usually adjusted to be in the range of 1-1000 mg depending on the efficacy of the selected active ingredient.

Those skilled in the art can determine a preferred dose suitable for a certain instance according to conventional method. In general, the initial treatment dose is lower than the optimal dose of the active ingredient, and then the dose of administration is increased gradually, until the optimal therapeutic effect is accomplished. For convenience, the total daily dose can be divided into several portions and administered for several times.

The application of deuterated thienopiperidine derivatives of the present invention or the pharmaceutically acceptable salt thereof is present in manufacturing drugs for treating and preventing cardiovascular and cerebrovascular diseases such as heart failure, stroke, and unstable angina, especially the application in manufacturing the anti-platelet aggregation drugs.

In another aspect, the present invention also provides a manufacturing method for deuterated thienopiperidine derivatives of the present invention or the pharmaceutically acceptable salt, solvate, polymorph, enantiomer or racemic mixture thereof, the manufacturing method comprising the following reaction steps:

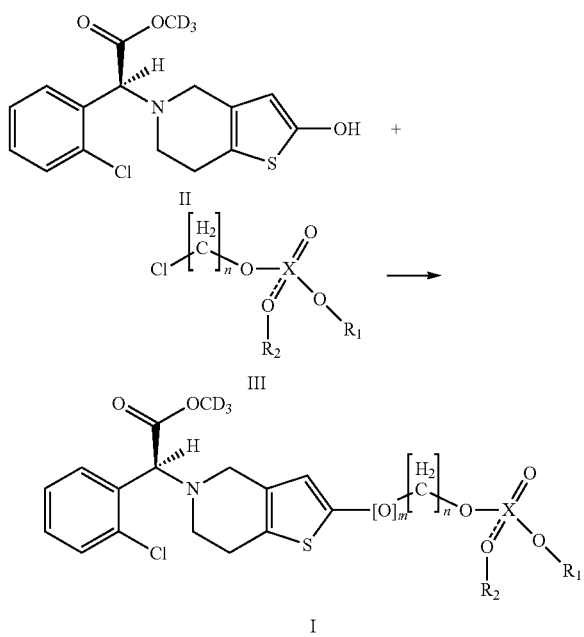

wherein the substituents are described previously.

According to the detailed embodiments of the present invention, compound TSD-9 of the present invention can be prepared in the following manner:

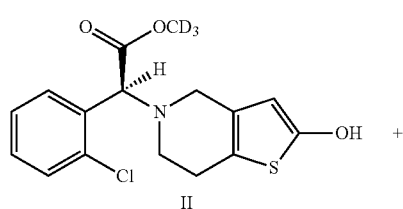

II

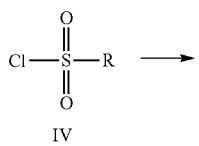

IV

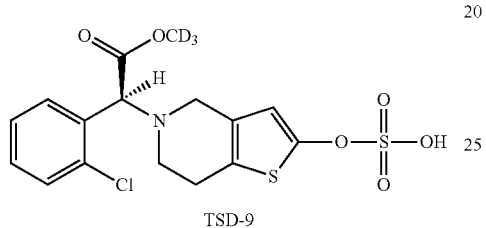

TSD-9 wherein, R is chlorine or hydroxyl.

DETAILED DESCRIPTION OF THE INVENTION

Figure 1:
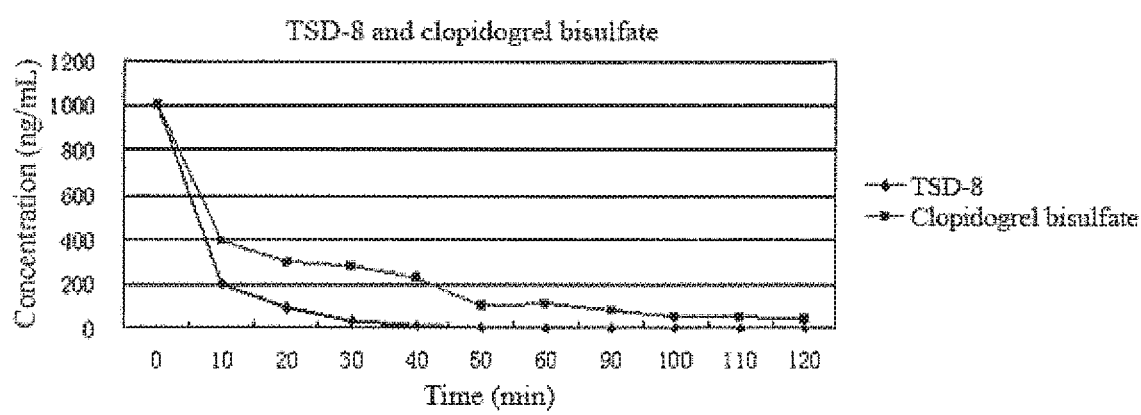
FIG. 1 is a diagram of the esterase hydrolysis rates of TSD-8 and clopidogrel.

The embodiments were used to further illustrate the present invention, but not intended to be limit.

Embodiment 1

Methyl-d3 (R)-o-chloromandelate

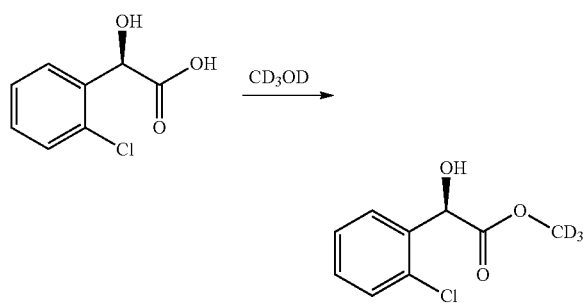

9.4 g of (R)-o-chloromandeic acid was dissolved in 36 mL of deuterated methanol, into which 1 mL of HCl/dioxane solution (4 M) was added, reflux heated for 5 hours, and the solvent was removed by evaporation under reduced pressure after cooling. The residue was dissolved with methylene chloride, and the resultant solution was washed sequentially with 5% aqueous potassium carbonate solution and water, and the methylene chloride solution was dried with anhydrous sodium sulfate. After removing the desiccant by filtration, the solution was evaporated to dryness to obtain 9.2 g of colorless transparent oily product methyl-d3 (R)-o-chloromandelate, with a yield of 89.7%.

Embodiment 2

Methyl-d3 (R)-2-(2-chlorophenyl)-2-(4-nitrophenylsulfonyloxy)-acetate (II-1)

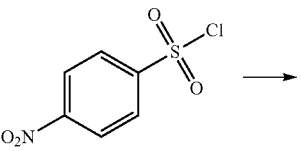

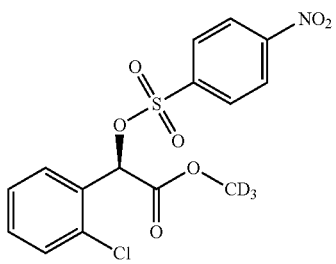

II-1

10.2 g of methyl-d3 (R)-o-chloromandelate was dissolved in 50 mL of anhydrous methylene chloride, into which 65.6 g of triethylamine and catalytic amount of DMAP was added, stirred, and cooled to 0° C. 50 mL anhydrous methylene chloride solution of 12.2 g p-nitrobenzenesulfonyl chloride was dropwise added at the same temperature to react for 4 hours at a constant temperature. 100 mL of water was added into the reaction solution, stirred, allowed to stand still to separate the liquid. The aqueous phase was extracted for three times with 150 mL of methylene chloride and dried with anhydrous sodium sulfate after combining the organic phases. The methylene chloride was dried out under reduced pressure after removing the desiccant by filtration to obtain 20.9 g of oily crude product in dark red. The resultant substance was recrystallized with methanol to give 15.8 g of solid product (II-1), with a yield of 81.3%.

Embodiment 3

Methyl-d3(2S)-2-(2-chlorophenyl)-2-(2-oxo-7,7a-dihydrothieno [3,2-c]pyridin-5(2H,4H,6H)-yl)-acetate (V-1)

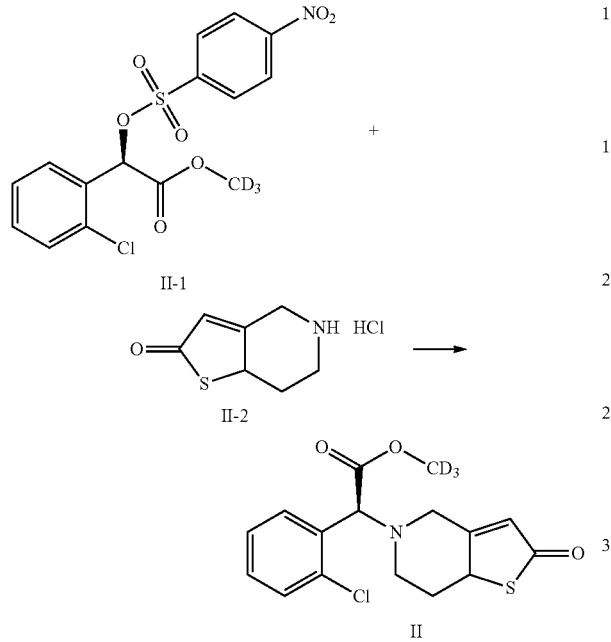

58.1 g (0.15 mol) of methyl-d3(R)-2-(2-chlorophenyl)-2-(4-nitrophenylsulfonyloxy)-acetate (II-1), 32.3 g (0.17 mol) of 5,6,7,7a-tetrahydrothieno[3,2-c]pyridin-2(4H)-hydrochloride (IV-1) and 37.8 g (0.38 mol) of potassium bicarbonate were combined into 500 mL acetonitrile, to react by stirring at room temperature for 26 hours with a system under protecting with nitrogen. The insoluble substances were filtered out from the reaction solution after standing still to obtain dark red mother liquor. The solvent was dried out under reduced pressure, passed through a flash chromatography (petroleum ether:ethyl acetate=4:1) to obtain 35.4 g of oily product with a yield of 70%.

Embodiment 4

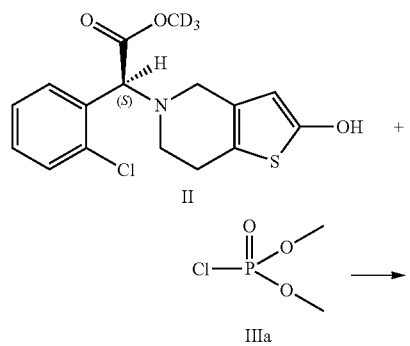

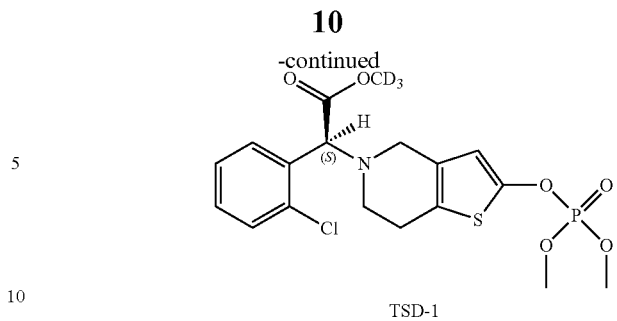

Deuterated 2-oxo-clopidogrel intermediate II (200 mg, 0.6 mmol) was dissolved in 5 mL of anhydrous tetrahydrofuran, cooled to −20° C., into which lithium diisopropylamide (2.0 M, 0.5 mL, 1 mmol) was added and stirred for 20 minutes. Compound IIIa (104 mg, 0.72 mmol) was added into the reaction solution, to react for 12 hours under self-heating process. The reaction was quenched with 4% hydrochloric acid, into which 50 mL of ethyl acetate was added, and the organic layer was washed with sodium bicarbonate and brine respectively, dried with anhydrous sodium sulfate, filtered and concentrated. Silica gel column chromatography (PE:EA=4:1) was purified to obtain compound TSD-1 (245 mg, yield: 92%).

$^1$H NMR (400 MHz, CDCl$_3$): δ 7.67-7.65 (m, 1H), 7.42-7.40 (m, 1H), 7.31-7.26 (m, 2H), 6.25 (d, 1H), 4.91 (s, 1H), 3.87 (s, 3H), 3.64-3.60 (m, 1H), 3.51-3.48 (m, 1H), 2.89-2.87 (m, 2H), 2.75-2.73 (m, 2H), MS: m/z 449 [M+1]$^+$.

Embodiment 5

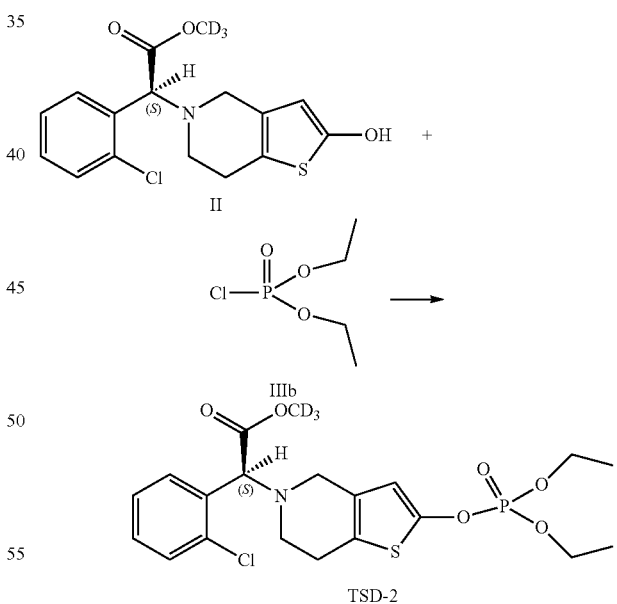

Deuterated 2-oxo-clopidogrel intermediate II (500 mg, 1.5 mmol) was dissolved in 10 mL of anhydrous tetrahydrofuran and cooled to −20° C., into which lithium diisopropylamide (2.0 M, 1.25 mL, 2.5 mmol) was added, stirred for 30 minutes. Compound IIIb (311 mg, 1.8 mmol) was added into the reaction solution to react for 12 hours under self-heating process. The reaction was quenched with 4% hydrochloric acid, into which 100 mL of ethyl acetate was added, and the organic layer was washed with sodium bicarbonate and brine respectively, dried with anhydrous sodium sulfate, filtered and concentrated. Silica gel column chromatography (PE:EA=4:1) was purified to obtain compound TSD-2 (660 mg, yield: 93%).

¹H NMR (400 MHz, CDCl₃): δ 7.69-7.66 (m, 1H), 7.43-7.41 (m, 1H), 7.33-7.28 (m, 2H), 6.27 (d, 1H), 4.91 (s, 1H), 4.27-4.18 (m, 4H), 3.65-3.61 (m, 1H), 3.52-3.49 (m, 1H), 2.90-2.87 (m, 2H), 2.76-2.74 (m, 2H), 1.39-1.36 (dt, 6H). MS: m/z 477 [M+1]⁺.

Embodiment 6

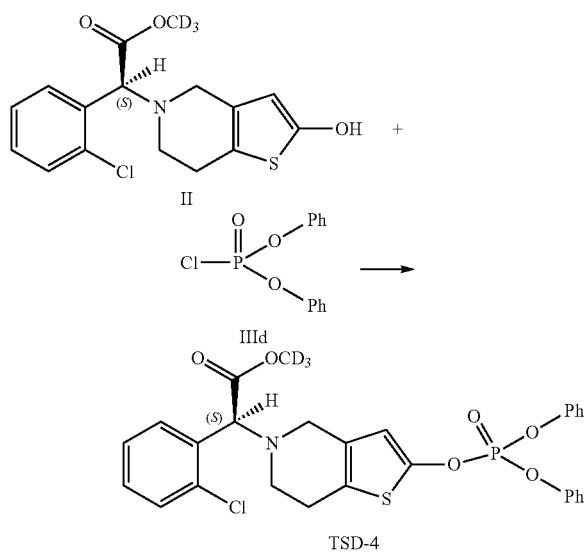

Deuterated 2-oxo-clopidogrel intermediate II (100 mg, 0.3 mmol) was dissolved in 5 mL of anhydrous tetrahydrofuran and cooled to −20° C., into which lithium diisopropylamide (2.0 M, 0.25 mL, 0.5 mmol) was added, stirred for 20 minutes. Compound IIId (97 mg, 0.36 mmol) was added into the reaction solution to react for 12 hours under self-heating process. The reaction was quenched with 4% hydrochloric acid, into which 50 mL of ethyl acetate was added, and the organic layer was washed with sodium bicarbonate and brine respectively, dried with anhydrous sodium sulfate, filtered and concentrated. Silica gel column chromatography (PE:EA=2:1) was purified to obtain compound TSD-4 (162 mg, yield: 95%).

¹H NMR (400 MHz, CDCl₃): δ 7.71-7.68 (m, 1H), 7.47-7.42 (m, 5H), 7.35-7.24 (m, 10H), 6.28 (d, 11H), 4.92 (s, 1H), 2.89-2.87 (m, 2H), 2.75-2.73 (m, 2H), MS: m/z 573 [M+1]⁺.

Embodiment 7

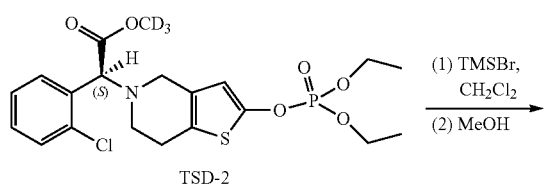

TSD-2 (500 mg, 1.04 mmol) was dissolved in 10 mL of dry methylene chloride, into which TMSBr (1.7 mL, 13 mmol) was added to react at room temperature for 12 h, the reaction was stopped, and the solvent was pumped out under reduced pressure, then 10 mL of methanol was added in and stirred for 1 h. The reaction solution was concentrated directly, silica gel column chromatography (n-butanol:formic acid:water=5:5:1) was purified to obtain compound TSD-6 (390 mg, yield: 90%).

¹H NMR (400 MHz, DMSO): δ 7.60 (d, 1H), 7.53 (d, 1H), 7.41-7.40 (m, 2H), 6.24 (s, 1H), 4.91 (s, 1H), 3.56 (s, 2H), 2.85 (brs, 2H), 2.66 (brs, 2H), MS: m/z 421 [M+1]⁺.

Embodiment 8

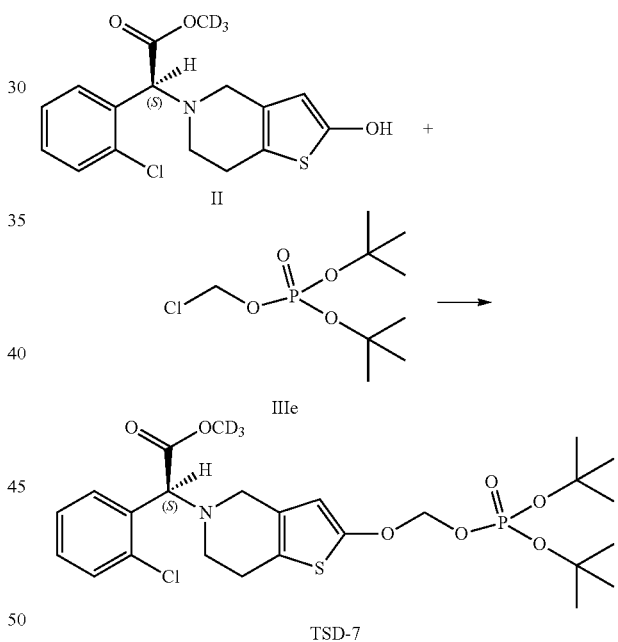

Deuterated 2-oxo-clopidogrel intermediate II (500 mg, 1.5 mmol) was dissolved in 5 mL of anhydrous tetrahydrofuran and cooled to −20° C., into which lithium diisopropylamide (2.0 M, 1.25 mL, 2.5 mmol) was added and stirred for 20 minutes. Compound IIIe (466 mg, 1.8 mmol) was added into the reaction solution to react for 12 hours under self-heating process. The reaction was quenched with 4% hydrochloric acid, into which 100 mL of ethyl acetate was added, and the organic layer was washed with sodium bicarbonate and brine respectively, dried with anhydrous sodium sulfate, filtered and concentrated. Silica gel column chromatography (PE:EA=2:1) was purified to obtain compound TSD-7 (269 mg, yield: 32%).

¹H NMR (400 MHz, CDCl₃): δ 7.69-7.65 (m, 1H), 7.42-7.40 (m, 1H), 7.31-7.24 (m, 2H), 6.17 (s, 1H), 5.46 (s,

1H), 5.43 (s, 1H), 4.91 (s, 1H), 3.64-3.60 (m, 1H), 3.50-3.47 (m, 1H), 2.91-2.88 (m, 2H), 2.75-2.72 (m, 2H), 1.50 (s, 18H). MS: m/z 560 [M+1]$^+$.

Embodiment 9

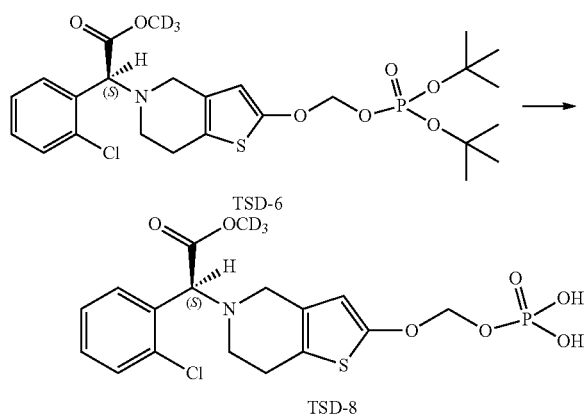

TSD-6 (500 mg, 0.89 mmol) was dissolved in 10 mL of methylene chloride, to which trifluoroacetic acid (2 mL) was added, stirred at room temperature for 1 h and concentrated under reduced pressure. Silica gel column chromatography (n-butanol:formic acid:water=5:5:1) was purified to obtain compound TSD-8 (140 mg, yield: 35%).

$^1$H NMR (400 MHz, DMSO): δ 7.62-7.60 (m, 1H), 7.54-7.41 (m, 3H), 6.18 (s, 1H), 5.84 (s, 1H), 5.37-5.32 (d, 2H), 4.26-3.98 (m, 2H), 3.74-3.66 (m, 2H), 3.15-3.00 (m, 2H), MS: m/z 451 [M+1]$^+$.

Embodiment 10

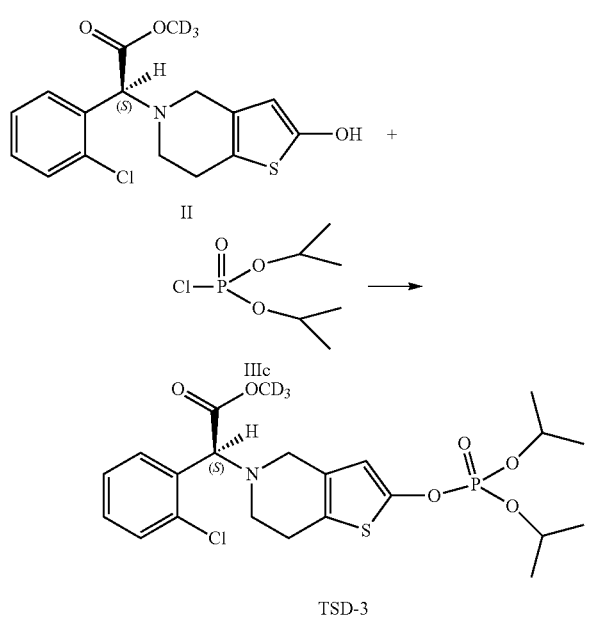

Deuterated 2-oxo-clopidogrel intermediate II (150 mg, 0.45 mmol) was dissolved in 5 ml of anhydrous tetrahydrofuran and cooled to −20° C., into which lithium diisopropylamide (2.0M, 0.4 mL, 0.8 mmol) was added and stirred for 20 minutes. Compound IIIc (108 mg, 0.54 mmol) was added into the reaction solution to react for 12 hours under self-heating process. The reaction was quenched with 4% hydrochloric acid, into which 50 mL of ethyl acetate was added, and the organic layer was washed with sodium bicarbonate and brine respectively, dried with anhydrous sodium sulfate, filtered and concentrated. Silica gel column chromatography (PE:EA=2:1) was purified to obtain compound TSD-3 (192 mg, yield: 85%).

1H NMR (400 MHz, CDCl$_3$): δ 7.68-7.67 (m, 1H), 7.41-7.39 (m, 1H), 7.34-728 (m, 2H), 6.28 (d, 1H), 4.92 (s, 1H), 4.74 (m, 211), 4.26-4.17 (m, 4H), 3.64-3.61 (m, 1H), 3.53-3.49 (m, 1H), 1.28 (d, 12H). MS: m/z 505 [M+1]$^+$.

Embodiment 11

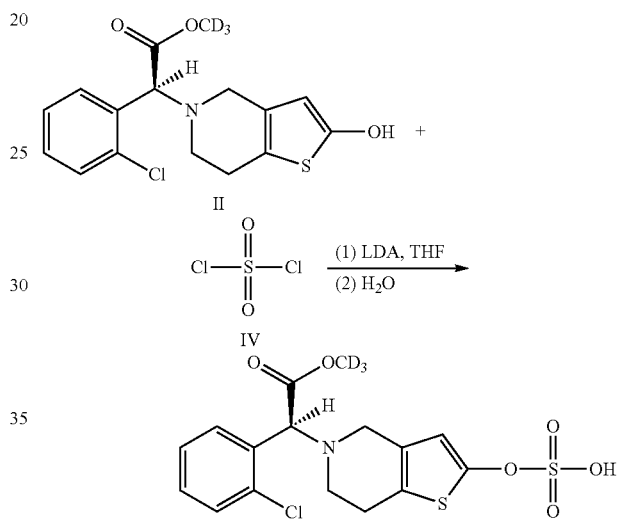

Deuterated 2-oxo-clopidogrel intermediate II (500 mg, 1.5 mmol) was dissolved in 5 mL of anhydrous tetrahydrofuran and cooled to −20° C., into which lithium diisopropylamide (2.0 M, 1.25 mL, 2.5 mmol) was added and stirred for 20 minutes. Compound IV was added into the reaction solution to react for 12 hours under self-heating process. The reaction was quenched with 4% hydrochloric acid, into which 100 mL of ethyl acetate was added, the organic layer was washed with sodium bicarbonate and brine respectively, dried with anhydrous sodium sulfate, filtered and concentrated. Silica gel column chromatography (PE:EA=2:1) was purified to obtain compound TSD-9 (269 mg, yield: 32%).

$^1$H NMR (400 MHz, CDCl$_3$): δ 7.69-7.65 (m, 1H), 7.42-7.40 (m, 1H), 7.31-7.24 (m, 2H), 6.17 (s, 1H), 5.46 (s, 1H), 5.43 (s, 1H), 4.91 (s, 1H), 3.64-3.60 (m, 1H), 3.50-3.47 (m, 1H), 2.91-2.88 (m, 2H), 2.75-2.72 (m, 2H), 1.50 (s, 18H). MS: m/z 563 [M+1]$^+$.

Embodiment 12: Drug Efficacy Study of the Compounds of the Present Invention

Experimental Method:

Addition of small dose of ADP (concentration less than 0.9 μmol/L) into the platelet suspension could lead to rapid platelet aggregation, followed by quick disaggregation; if moderate dose of ADP (about 1.0 μmol/L) was added, then the second irreversible aggregation phase appeared not long after the end of the first aggregation phase and the disaggregation. The maximum aggregation rate of the irreversible aggregation phase was used to evaluate the effect of the test samples on the function of blood coagulation. The present experiment used the semi-automatic Platelet Aggregation Analyzer Model NJ4 from Precil to observe the inhibitive effect of the test samples provided by the Tasly Group on the platelet aggregation.

Experimental Materials:

Animals: Wistar male rats, weighing 230-250 g, were purchased from Vital River Laboratory Animal Technology Co., Ltd.

Reagent: ADP, Sigma Corporation.

Test samples: 16 test samples were provided by the Tasly Group; referred to China patent application 201310428052.4 for manufacturing method of TSC-1~4 and TSC-6~9.

Dose of administration: the test samples were suspended with 0.25% CMC, administered 3 mg/kg weight, volume of administration: 2 mL.

Experimental Procedure:

2 Hours after administration, the rats were anesthetized with pentobarbital sodium, and blood was drawn from the abdominal aorta, anticoagulated with sodium citrate with a ratio of 1:9, and centrifuged to obtain the platelet-rich plasma and platelet-poor plasma, with the mixed ratio of the platelet-poor plasma to platelet-rich plasma=3:1.

Experimental Results:

TABLE 1

Effects of the compounds of the present invention on the maximum aggregation rate of the ADP induced platelet aggregation

| Group | Dose of Administration mg/kg | n | Maximum Platelet Aggregation Rate |
|---|---|---|---|
| control | — | 5 | 61.22 ± 4.73 |
| clopidogrel | 3 | 5 | 46.77 ± 8.28* |
| prasugrel | 3 | 5 | 20.72 ± 8.84* |
| TSC-1 | 3 | 2 | 45.8 ± 3.55* |
| TSC-2 | 3 | 3 | 41.7 ± 7.43* |
| TSC-3 | 3 | 3 | 38.7 ± 4.27* |
| TSC-4 | 3 | 3 | 46.5 ± 8.16* |
| TSC-6 | 3 | 3 | 29.6 ± 5.33* |
| TSC-7 | 3 | 3 | 39.2 ± 6.16* |
| TSC-8 | 3 | 5 | 30.6 ± 4.22* |
| TSC-9 | 3 | 3 | 25.7 ± 3.25* |
| TSD-1 | 3 | 5 | 35.6 ± 3.35* |
| TSD-2 | 3 | 5 | 32.7 ± 5.33* |
| TSD-3 | 3 | 5 | 28.4 ± 3.27* |
| TSD-4 | 3 | 5 | 36.2 ± 4.16* |
| TSD-6 | 3 | 5 | 17.4 ± 5.13* |
| TSD-7 | 3 | 5 | 27.1 ± 6.21* |
| TSD-8 | 3 | 5 | 16.3 ± 4.16* |
| TSD-9 | 3 | 5 | 18.7 ± 4.12* |

*$P < 0.001$ compared with the normal group.

In the ADP induced platelet aggregation experiment, each of the test samples had the significant effect of inhibiting the rat platelet aggregation, and could reverse the second phase platelet aggregation, leading to disaggregation. Moreover, the effects of inhibiting the platelet aggregation of the series of deuterated thienopiperidine derivatives of the present invention (TSD-1~4, 6~9) were much better than those of the series of non-deuterated thienopiperidine derivatives (TSC-1~TSC-4, TSC-6~TSC~9).

Embodiment 13

Comparison Test of the Esterase Hydrolysis Rates of the Compound of Formula TSD-8 and Clopidogrel The hydrolysis rates of formula TSD-8 and clopidogrel bisulfate in the rat whole blood were determined by employing the in vitro incubation method.

3 mL of rat fresh whole blood was taken and placed in a glass test tube. 30 μg/mL of TSD-8 and clopidogrel bisulfate (prepared with saline) were added, with 3 parallel tests for each group. The test tubes were shocked at a constant temperature of 37° C., 100 μL of the mixture was taken out at fixed time points of 10 min, 20 min, 30 min, 40 min, 50 min, 60 min, 70 min, 80 min, 90 min, 100 min, 110 min, and 120 min, 900 μL of methanol was added to stop the reaction immediately, then 100 μL methanol/water (1:1, v/v) and 100 μL internal standard (diazepam, 100 ng/mL) were added sequentially. The mixture was centrifuged at 13000 rpm at low temperature for 10 min, the supernatant was transferred into another EP tube, and 20 μL of the supernatant was taken for sample injection.

TABLE 2

Comparison test of the esterase hydrolysis rates of TSD-8 and clopidogrel bisulfate

| Time (min) | Num. 1 | Num. 2 | Num. 3 | Mean |
|---|---|---|---|---|
| TSD-8 sample test results | | | | |
| 10 | 531 | 252 | N/A | 391.50 |
| 20 | 336 | 242 | 292 | 290.00 |
| 30 | 255 | 291 | 280 | 275.33 |
| 40 | 222 | 219 | 228 | 223.00 |
| 50 | 112 | 103 | 90 | 101.67 |
| 60 | 115 | 123 | 98 | 112.00 |
| 90 | 76.3 | 77.4 | 70.2 | 74.63 |
| 100 | 52.7 | 63.2 | 50.3 | 55.40 |
| 110 | 45.7 | 51.5 | 46.5 | 47.90 |
| 120 | 34.3 | 38.7 | 31.7 | 34.90 |
| Clopidogrel bicarbonate sample test results | | | | |
| 10 | 232 | N/A | 167 | 199.50 |
| 20 | 64.1 | 131 | 76.5 | 90.53 |
| 30 | 20.6 | 53 | 28.6 | 34.07 |
| 40 | 6.46 | 14.3 | 14.7 | 11.82 |
| 50 | 0.479 | 1.01 | 0.359 | 0.62 |
| 60 | 0.347 | 1.24 | 0 | 0.53 |
| 90 | 0 | 0 | 0 | 0.00 |
| 100 | 0 | 0 | 0 | 0.00 |
| 110 | 0 | 0 | 0 | 0.00 |
| 120 | 0 | 0 | 0 | 0.00 |

N/A indicates lack of data, the same below.

It could be seen from FIG. 1 that the concentration of TSD-8 at each time point was greater than that of clopidogrel, the hydrolysis rate of TSD-8 in the rat whole blood was therefore slower than that of clopidogrel, and at around 50 min the concentration of clopidogrel bisulfate in the whole blood was already lower than the quantitative lower limit, while that of the compound of formula TSD-8 could still be detected.

Embodiment 14

Comparison Test of the Esterase Hydrolysis Rates of the Compound of Formula TSD-6 and Clopidogrel The hydrolysis rates of formula TSD-6 and clopidogrel bisulfate in the rat whole blood were determined by employing the in vitro incubation method.

3 mL of the rat fresh whole blood was taken and placed in a glass test tube. 30 μg/mL of formula TSD-6 and clopidogrel bisulfate (prepared with saline) were added, with 3 parallel tests for each group. The test tubes were shocked at a constant temperature of 37° C., 100 µL of the mixture was taken out at fixed time points of 10 min, 20 min, 30 min, 40 min, 50 min, 60 min, 70 min, 80 min, 90 min, 100 min, 110 min, and 120 min, into which 900 µL of methanol was added to stop the reaction immediately, then 100 µL methanol/water (1:1, v/v) and 100 µL internal standard (diazepam, 100 ng/mL) were added sequentially. The mixture was centrifuged at 13000 rpm at low temperature for 10 min, the supernatant was transferred into another EP tube, and 20 µL of the supernatant was taken for sample injection.

TABLE 3

Comparison test of the esterase hydrolysis rates of TSD-6 and clopidogrel bisulfate

| Time (min) | Num. 1 | Num. 2 | Num. 3 | Mean |
|---|---|---|---|---|
| TSD-6 sample test results | | | | |
| 10 | 486 | 287 | 396 | 389.7 |
| 20 | 306 | 345 | 295 | 315.3 |
| 30 | 246 | 223 | 264 | 244.3 |
| 40 | 232 | 213 | 208 | 217.7 |
| 50 | 196 | 153 | 167 | 172.0 |
| 60 | 115 | 134 | 148 | 132.3 |
| 90 | 85.3 | 112 | 95.2 | 97.50 |
| 100 | 84.7 | 71.8 | 61.2 | 72.57 |
| 110 | 48.1 | 59.1 | 56.7 | 54.63 |
| 120 | 24.5 | 28.4 | 24.6 | 25.83 |
| Clopidogrel bisulfate sample test results | | | | |
| 10 | 238 | 221 | 174 | 211.0 |
| 20 | 66.2 | 128 | 74.7 | 89.6 |
| 30 | 24.1 | 57.2 | 24.1 | 35.1 |
| 40 | 6.27 | 15.1 | 19.3 | 11.2 |
| 50 | 0.449 | 1.12 | 0.518 | 0.70 |
| 60 | 0.417 | 1.45 | 0 | 0.62 |
| 90 | 0 | 0 | 0 | 0 |
| 100 | 0 | 0 | 0 | 0 |
| 110 | 0 | 0 | 0 | 0 |
| 120 | 0 | 0 | 0 | 0 |

Figure 2:
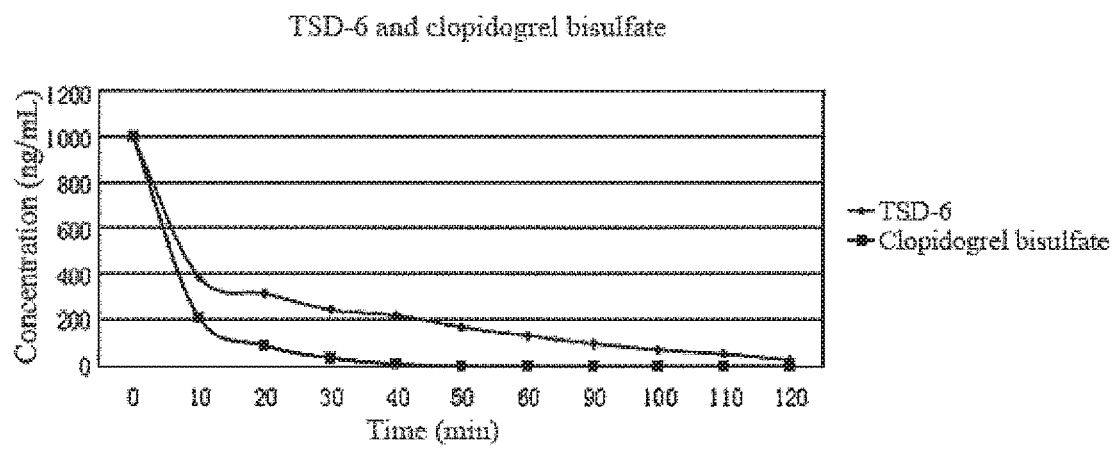
FIG. 2 is a diagram of the esterase hydrolysis rates of TSD-6 and clopidogrel.

It could be seen from FIG. 2 that the concentration of TSD-6 at each time point was greater than that of clopidogrel, the hydrolysis rate of TSD-6 in the rat whole blood was significantly slower than that of clopidogrel, and at around 50 min the concentration of clopidogrel bisulfate in the whole blood was already lower than the quantitative lower limit, while that of the compound of formula TSD-6 could still be detected.

Embodiment 15

Comparison of the pharmacokinetics of formula TSD-6, TSC-6, I-1 and clopidogrel for the in-vivo metabolization into 2-oxo-clopidogrel in rats; the compound structures are present as shown in the following figure:

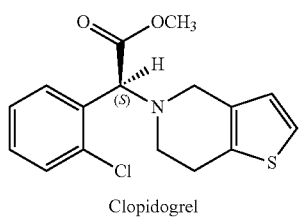

Clopidogrel

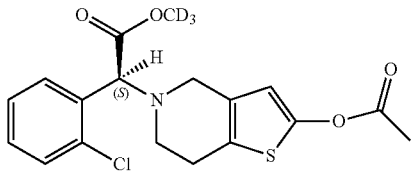

I-1

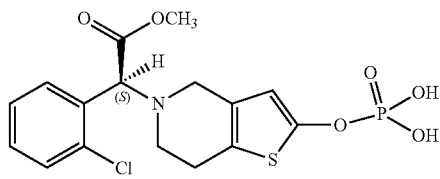

TSC-6

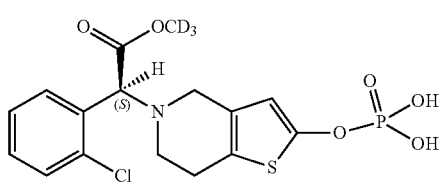

TSD-6

Test Animals:

24 male SD rats, 6-7 weeks old, animal weighing 240~290 g, were purchased from Shanghai Slac Laboratory Animal Co., Ltd., with animal certificate number of 2015000514648. Before the test, the animal should be fed for at least 3 days to adapt to the environment. The animals of the intravenous injection (IV) group were not fasted; the animals of the oral gavage (PO) group were fasted overnight before administration and fed 4 hours after administration; the animals were allowed to drink water freely throughout the test.

Test Drugs:

clopidogrel bisulphate (Clopidogrel), TSC-6, I-1 and TSD-6, provided by Tasly.

Grouping of animals and the sampling time points: 24 SD rats were divided into 8 groups, 3 for each group, the animals of the intravenous injection group were administered with 3 mg/kg of the test drugs through the dorsal venous of foot, and the animals of the oral gavage group were administered with 15 mg/kg of the test drugs through gavage. See table 4 for the administration scheme.

TABLE 4

The animal administration and blood sampling scheme

| Group | Test Sample | n | Dose of Administration (mg/kg) | volume of Administration (ml/kg) | Administration Route | Sampling Time |
|---|---|---|---|---|---|---|
| Group 1 | Clopidogrel | 3 | 3 | 1 | intravenous injection | Intravenous injection: the plasma was collected at pre-dose, and 5 min, 15 min, 30 min, 1 hr, 2 hr, 4 hr, 8 hr, and 24 hr after administration respectively, 9 time points overall. Oral gavage: the plasma was collected at pre-dose and 15 min, 30 min, 1 hr, 2 hr, 4 hr, 8 hr, and 24 hr after the administration respectively, 8 time points overall. |
| Group 2 | Clopidogrel | 3 | 15 | 10 | oral gavage | |
| Group 3 | TSC-6 | 3 | 3 | 1 | intravenous injection | |
| Group 4 | TSC-6 | 3 | 15 | 10 | oral gavage | |
| Group 5 | I-1 | 3 | 3 | 1 | intravenous injection | |
| Group 6 | I-1 | 3 | 15 | 10 | oral gavage | |
| Group 7 | TSD-6 | 3 | 3 | 1 | intravenous injection | |
| Group 8 | TSD-6 | 3 | 15 | 10 | oral gavage | |

Sample Collection and Storage:

According to the predetermined time points, the corresponding animals were fixed, about 80 µL of blood was sampled via the tail vein, the blood sample was anticoagulated with sodium heparin and placed on the wet ice. 60 µL of the blood sample was taken immediately and added into 600 µL of internal standard solution (40 ng/mL diclofenac acetonitrile solution, with 0.1% formic acid), and the mixture was vortexed for 0.5 min and centrifuged at 12000 rpm at 4° C. for 5 min to obtain a supernatant. The supernatant sample was firstly placed in the dry ice for frozen storage, and then transferred into a refrigerator at −70° C. for long-term storage until being analyzed.

Test Results:

Animal number: 30

Feeding Condition:
fed in the animal room of clean grade, temperature 20.5-22.5° C., humidity 50-65%, light 150-250 Lx, 12 hours of day and night's alteration (6:00-18:00 as the day.)

Test Samples, Control Drug and Preparation Method:
compounds TSC-6, I-1, TSD-6 and clopidogrel were dissolved in 5 mL 0.25% CMC, ultrasonic treated at 37° C. for 20 min, and stirred into a suspension with a stirrer.

Dose Setting and its Reason:
dose for the test compounds TSC-6, I-1, TSD-6 was 1 mg/kg. Dose of administration for the positive compound clopidogrel was 10 mg/kg, determined on the basis of references and the test results of the present laboratory.

| PK parameters | Unit | Clopidogrel | | TSC-6 | | I-1 | | TSD-6 | |
|---|---|---|---|---|---|---|---|---|---|
| | | IV | PO | IV | PO | IV | PO | IV | PO |
| Tmax | hr | 0.083 | 0.5 | 0.083 | 0.333 | 0.083 | 0.333 | 0.083 | 0.333 |
| Cmax | ng/mL | 19.1 | 2.23 | 150 | 15.4 | 120 | 10.9 | 307 | 27.7 |
| Auc$_{(0-t)}$ | hr*ng/mL | 18 | 7.74 | 73 | 27.2 | 75 | 14.6 | 116 | 46.4 |
| Terminal$_{t1/2}$ | hr | 0.525 | NA | 0.683 | 0.622 | 0.541 | 0.614 | 0.787 | 0.76 |

It could be seen from the comparison study of the pharmacokinetics of the key metabolite 2-oxo-clopidogrel that the exposure amount of the key metabolic intermediate of the deuterated compound TSD-6 developed was evidently higher than that of the non-deuterated compound TSC-6 and similar compound I-1 of the same kind for both oral and intravenous injection administrations. The pharmacokinetic data exhibited a better unique metabolic characteristic of TSD-6, which will be advantageous to improve the drug effect and overcome the disadvantages of the prior compounds.

Embodiment 16

Comparison Study on the Drug Effects of Formula TSC-6, I-1, TSD-6 and Clopidogrel in the Rat Tail Bleeding Model Animals and Feeding:
genus, strain SD rat,
Provider: Slac
Weight: 250-350 g
Sex: male Administration Route:
oral gavage.

Experimental Method:
The animals were allowed adapt to the environment after arrival for 1 week and fasted for 16 hours prior to the experiment.
The tail bleeding time started to be recorded 2 h after oral administration of the test compounds and 4 h after oral administration of clopidogrel.
The rats were anesthetized with pentobarbital sodium (50 mg/kg, ip) 10 min prior to the recording of the tail bleeding time, after the rat was completely anesthetized and reaching the detection time, the tail was cut at 1.3 mm from the rat tail-tip with a scissor and perpendicularly immerged into a saline at 37° C. Timing recording was not started until the blood flow appeared.
The timing recording was stopped when the bleeding time interval was longer than 20 seconds. The maximum observation time for the blood flow was set for 40 minutes. If it was longer than 40 minutes, the timing recording was stopped and the time was recorded as 40 minutes.

Test Results

| Entry | Compound | Dose (mg/kg) | Tail Bleeding Time (s) |
|---|---|---|---|
| 1 | Vehicle | — | 158 |
| 2 | TSC-6 | 1.0 | 635 |
| 3 | I-1 | 1.0 | 950 |
| 4 | TSD-6 | 1.0 | 1331* |
| 5 | Clopidogrel | 10 | 1896*** |

*$P < 0.05$,
***$P < 0.001$ vs Vehicle

The anticoagulant effects of compounds were evaluated by comparing the tail bleeding time in the rat tail bleeding model between TSC-6, I-1, TSD-6 and clopidogrel. It could be seen that the anticoagulant effect of the deuterated compound TSD-6 developed by inventors was much better than that of the non-deuterated compound TSC-6 and analog I-1 of the same kind, demonstrating the unique anticoagulant activity of TSD-6.

Embodiment 17

Comparison Study on the Drug Effects of TSC-6, I-1, TSD-6 and Clopidogrel in the Rat Arteriovenous Thrombus Loop Model
Animals and Feeding:
genus, strain: SD rat,
Provider: Slac
Weight: 250-350 g
Sex: male
Animal number: 30
Feeding Condition:
fed in the animal room of clean grade, temperature 20.5-22.5° C., humidity 50-65%, light 150-250 Lx, 12 hours of day and night's alteration (6:00-18:00 as the day.)
Test Samples, Control Drug and Preparation Method:
compounds TSC-6, I-1, TSD-6 and clopidogrel were dissolved in 5 mL of 0.25% CMC, ultrasonic treated at 37° C. for 20 min, and stirred into a suspension with a stirrer.
Dose Setting and its Reason:
dose for the test compounds TSC-6, I-1, and TSD-6 was 1 mg/kg. Dose of administration for the positive compound clopidogrel was 10 mg/kg, determined on the basis of references and the test results of the present laboratory.
Administration Route:
oral gavage.
Apparatus and Materials
Swab, dry tampon, alcohol pad, anerdian tampon.
Surgical scissor, ophthalmic forceps, hemostatic forceps, microsurgical scissor, microsurgical forceps, artery clamps.
3-0 surgical suture, thick PE tube (I.D.*O.D.=1.14 mm*1.63 mm, 8 cm long), think PE tube (I.D.*O.D.=0.72 mm*1.22 mm, 6 cm long).
Surgical board, binding rope, timer, precise electronic balance, weighing paper.
Syringe, normal saline.
7. Experimental Method
After arrival, the animals were let adapt to the environment for 1 week and fasted for 16 hours prior to the test.
The arteriovenous blood loop circulation was started 2 h after oral administration of the test compounds and 4 h after oral administration of clopidogrel.
The rats were anesthetized with pentobarbital sodium (50 mg/kg, ip) 15 min before the arteriovenous blood loop circulation was started.

The left external jugular vein and the right carotid artery were separated and inserted with thin PE tubes respectively.
Two PE tubes were connected with another thick PE tube with a length of 8 cm to form a circulation passage. There's a 6 cm surgical suture (3-0) in the thick PE tube.
15 min after the circulation passage was opened, the blood flow was blocked, the filament was taken out and weighed after the blood was sucked out. The thrombus weight was obtained after subtraction of the weight of the filament itself.
Test Results:

| Entry | Compound | Dose (mg/kg) | Thrombus (mg) |
|---|---|---|---|
| 1 | Vehicle | — | 52.2 |
| 2 | TSC-6 | 1.0 | 31.4* |
| 3 | I-1 | 1.0 | 25.6 |
| 4 | TSD-6 | 1.0 | 18.4* |
| 5 | Clopidogrel | 10 | 20.1** |

*$P < 0.01$,
**$P < 0.01$ vs Vehicle

The anticoagulant effects of the compounds were evaluated by comparing different weights of the thrombus formed by TSC-6, I-1, TSD-6 and clopidogrel in the rat arteriovenous thrombus loop model. It could be seen that the weight of the thrombus formed by the deuterated compound TSD-6 developed by inventors was much lower than that of the non-deuterated compound TSC-6 and analog I-1 of the same kind, demonstrating the unique anticoagulant activity of TSD-6.

The invention claimed is:

1. A deuterated thienopiperidine derivative consisting of TSD-6 or TSD-8

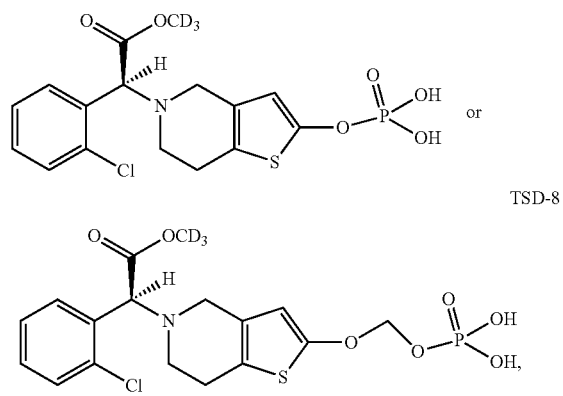

or a pharmaceutically acceptable salt thereof.

2. The deuterated thienopiperidine derivative of claim 1, wherein the pharmaceutically acceptable salt is prepared with an acid selected from the group consisting of sulfuric acid, hydrochloric acid, hydrobromic acid, phosphoric acid, tartaric acid, fumaric acid, maleic acid, citric acid, acetic acid, formic acid, methanesulfonic acid, p-toluenesulfonic acid, oxalic acid, and succinic acid.

3. A pharmaceutical composition, comprising the deuterated thienopiperidine derivative of claim 1.

4. The pharmaceutical composition of claim 3, further comprising a pharmaceutically acceptable carrier.

* * * * *